United States Patent [19]
O'Lenick, Jr.

[11] Patent Number: 5,908,949
[45] Date of Patent: Jun. 1, 1999

[54] ALKOXYLATED SILICONE SALICYLATE ESTERS

[75] Inventor: Anthony J. O'Lenick, Jr., Lilburn, Ga.

[73] Assignee: Lambent Technologies Inc, Norcross, Ga.

[21] Appl. No.: 09/040,431

[22] Filed: Mar. 18, 1998

[51] Int. Cl.$^6$ .................................................. C07F 7/08
[52] U.S. Cl. ........................................... 556/437; 556/440
[58] Field of Search ..................................... 556/440, 437

[56] References Cited

U.S. PATENT DOCUMENTS

| | | | |
|---|---|---|---|
| 5,296,625 | 3/1994 | O'Lenick, Jr. et al. ................. | 556/437 |
| 5,523,445 | 6/1996 | O'Lenick, Jr. ....................... | 556/440 X |
| 5,733,533 | 3/1998 | O'Lenick, Jr. ....................... | 556/440 X |

*Primary Examiner*—Paul F. Shaver

[57] ABSTRACT

The invention discloses novel alkoxylated salicylate esters of silicone compounds which contain an ester linkage, a polyoxyalkylene portion and a silicone polymer portion. Compounds of the invention are made by reacting (a) an alkoxylated carboxy silicone, and (b) salicylic acid to form an ester. Compounds of the invention by virtue of (i) the silicone group, (ii) the ester group and (iii) the ultra violet absorbing group salicylic, the compounds are effective durable ultra violet absorbers. The presence of the polyoxyalkylene portion of the molecule allows for the modification of the solubilities of the molecule in a variety of polar and non-polar solvents.

16 Claims, No Drawings

ALKOXYLATED SILICONE SALICYLATE ESTERS

BACKGROUND OF THE INVENTION

1. Field of the Invention

The invention discloses novel alkoxylated salicylate esters of silicone compounds which contain an ester linkage, a polyoxyalkylene portion and a silicone polymer portion in the same molecule. Compounds of the invention are made by reacting (a) an alkoxylated carboxy silicone, and (b) salicylic acid to form an ester. Compounds of the invention by virtue of (i) the silicone group, (ii) the ester group and (iii) the ultra violet absorbing group salicylic, the compounds are effective durable ultra violet absorbers. The presence of the polyoxyalkylene portion of the molecule allows for the modification of the solubilities of the molecule in a variety of polar and non-polar solvents.

The reaction used to prepare the compounds of the present invention is an esterification of a carboxy silicone and salicylic acid. The resulting ester provides ultra violet absorbance and is durable to substrates like textile fabrics, hair and skin.

2. Arts and Practices

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water. The presence of the polyoxyalkylene portion of the molecule allows for the modification of the solubilities of the molecule in a variety of polar and non-polar solvents.

Silicone oils do not provide ultra violet absorption, and consequently protection from the damaging effects of the sun. The aromatic compounds that provide this type of absorbance are not durable to the surfaces of substrates.

Silicone carboxy compounds have been described in U.S. Pat. No. 5,296,625 to O'Lenick, incorporated herein by reference.

THE INVENTION

OBJECT OF THE INVENTION

It is the object of the present invention to provide a durable ultra violet protection to substrates like skin, hair and textile fabrics and fibers, as well as rubber and plastics and a material that can be formulated in a variety of polar and non-polar solvents. The presence of silicone in the molecule gives superior durability to these substrates, the presence of the salicylic group gives superior ultra violet protection and the introduction of the ester linkage between the silicone and aromatic group results in a linkage which will biodegrade rapidly in waste water, making the compound less persistent in the waste water stream.

The formation of the ester linkage and the incorporation of the salicylic group into the silicone of the present invention is accomplished by an esterification reaction of a carboxy silicone and salicylic acid.

SUMMARY OF THE INVENTION

The compounds of this invention are made by the esterification of a carboxy silicone compound and salicylic acid. In order to obtain a molecule with the desired attributes, the aromatic compound must be mono-hydroxyl. This prevents crosslinking with the carboxy silicone, and formation of a polyester. The polyester is undesirable. The second requirement is that the aromatic compound chosen must have ultra violet absorbance. Salicylic acid meets both requirements.

Only if the compounds are specifically selected will compounds useful in the preparation of the compounds of the present invention be obtained.

Specifically, the compounds of the present invention are esters compounds which is prepared by the esterification reaction of;

(a) a silicone carboxylate conforming to the following structure:

$$R^e-\underset{\underset{Me}{|}}{\overset{\overset{Me}{|}}{Si}}-O-\left[\underset{\underset{R}{|}}{\overset{\overset{Me}{|}}{Si}}-O\right]_o-\left[\underset{\underset{R^1}{|}}{\overset{\overset{Me}{|}}{Si}}-O\right]_q-\underset{\underset{Me}{|}}{\overset{\overset{Me}{|}}{Si}}-R^e$$

wherein; Me is methyl; R and R" are selected from methyl and $$-(CH_2)_3-O-(EO)_a-(PO)_b-(EO)_c-C(O)-R''-C(O)-OH;$$

with the proviso that both R and R" are not methyl; R" is selected from $$-CH_2-CH_2-;\quad -CH_2-C(R^7)-H;\quad \text{[benzene ring]} \text{ and}$$

[tetrachlorobenzene structure]

$R^7$ is alkyl having from 1 to 20 carbon atoms;
$R^1$ is selected from lower alkyl $CH_3(CH)_n$— or phenyl; n is an integer from 0 to 8; a, b and c are integers independently ranging from 0 to 20;
EO is—$(CH_2CH_2-O)$—; PO is—$(CH_2CH(CH_3)-O)$—; o is an integer ranging from 1 to 100; q is an integer ranging from 0 to 500; and (b) salicylic acid which conforms to the following structure:

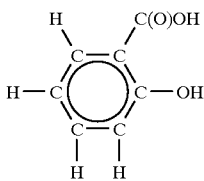

Compounds of the present invention conform to the following structure:

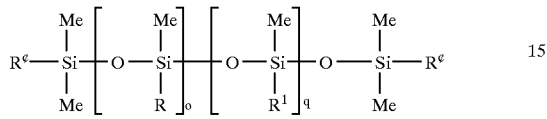

wherein; Me is methyl; R and R' are selected from methyl and

—(CH$_2$)$_3$—O—(EO)$_a$—(PO)$_b$—(EO)$_c$—C(O)—R"—C(O)—OR$^4$;

with the proviso that both R and R' are not methyl; R" is selected from

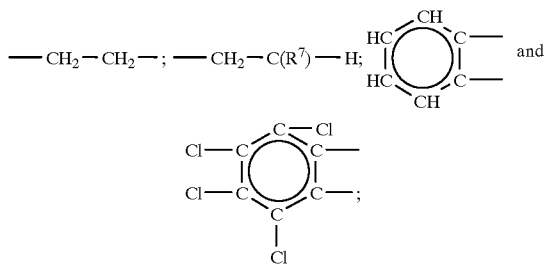

R$^7$ is alkyl having from 1 to 20 carbon atoms;
R$^1$ is selected from lower alkyl CH$_3$(CH)$_n$— or phenyl; n is an integer from 0 to 8; a, b and c are integers independently ranging from 0 to 20;
EO is—(CH$_2$CH$_2$—O)—; PO is—(CH$_2$CH(CH$_3$)—O)—; o is an integer ranging from 1 to 100; q is an integer ranging from 0 to 500;
R$^4$ is

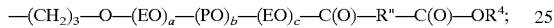

PREFERRED EMBODIMENT

In a preferred embodiment R" is—CH$_2$—CH$_2$—.

In another preferred embodiment R" is—CH$_2$—C(R$^7$)—H.

In another preferred embodiment R" is

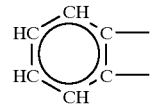

In another preferred embodiment R" is

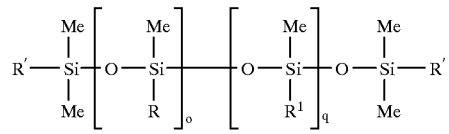

In another preferred embodiment R$^7$ is alkyl having from 6 to 20 carbon atoms.

In another preferred embodiment R$^7$ is alkyl having from 12 to 20 carbon atoms.

In another preferred embodiment R' is methyl.

In another preferred embodiment R' is

—(CH$_2$)$_3$—O—(EO)$_a$—(PO)$_b$—(EO)$_c$—C(O)—R"—C(O)—OR$^4$.

EXAMPLES

The compounds of the present invention are prepared by the reaction of a carboxy silicone compound and salicylic acid. Examples of suitable reactants are as follows;

All percentages given are based upon percent by weight, based upon the total weight of the entire batch. All temperatures are degrees C.

Reactants

Salicylic Acid Salicylic acid is 2-hydroxybenzoic acid.

Carboxy Functional Silicone Compounds

Carboxy Silicone Polymers are compounds available commercially form Lambent Technologies Inc. of Norcross, Ga. They are the topic of U.S. Pat. No. 5,296,625 to O'Lenick, incorporated herein by reference.

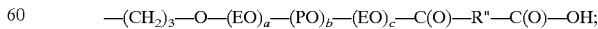

wherein; Me is methyl; R and R' are selected from methyl and

—(CH$_2$)$_3$—O—(EO)$_a$—(PO)$_b$—(EO)$_c$—C(O)—R"—C(O)—OH;

with the proviso that both R and R' are not methyl; R" is selected from

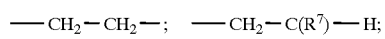

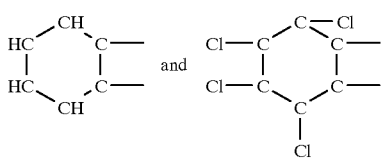

$R^7$ is alkyl having from 1 to 20 carbon atoms;
R1 is selected from lower alkyl $CH_3(CH)_n$— or phenyl; n is an integer from 0 to 8; a, b and c are integers independently ranging from 0 to 20;
EO is—$(CH_2CH_2$—$O)$—; PO is—$(CH_2CH(CH_3)$—$O)$—; o is an integer ranging from 1 to 100; q is an integer ranging from 0 to 500.

R" Definition

I) O'Lenick Reactant Example I (Succinic Anhydride)

R" is—$H_2C$—$CH_2$—

II) O'Lenick Reactant Example II (Alkyl Succinic Anhydride)

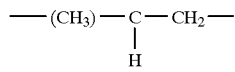

III) O'Lenick Reactant Example III (Alkyl Succinic Anhydride)

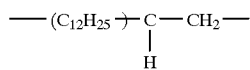

IV) O'Lenick Reactant Example IV (Alkyl Succinic Anhydride)

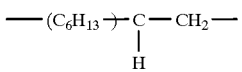

V) O'Lenick Reactant Example V (Alkyl Succinic Anhydride)

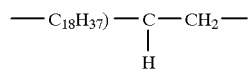

VI) O'Lenick Reactant Example VI (Alkyl Succinic Anhydride)

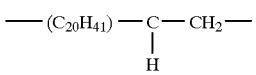

VII) O'Lenick Reactant Example VII (Maleic Anhydride)

R" is—HC=CH—

VIII) O'Lenick Reactant Example VIII (Phthalic Anhydride)

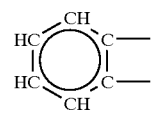

IX) O'Lenick Reactant Example IX (Tetrachlorophthalic anhydride)
R" is

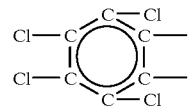

| Example | O'Lenick Example (U.S. PAT. 5,296,625) |
|---------|----------------------------------------|
| 1  | 15 |
| 2  | 16 |
| 3  | 17 |
| 4  | 18 |
| 5  | 19 |
| 6  | 20 |
| 7  | 21 |
| 8  | 22 |
| 9  | 23 |
| 10 | 24 |
| 11 | 25 |
| 12 | 26 |
| 13 | 27 |
| 14 | 28 |

COMPOUNDS OF THE PRESENT INVENTION

General Reaction Conditions

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc.. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

General Procedure

Into a suitable round bottom, three neck flask equipped with a Dean Stark trap, a thermometer and a nitrogen sparge is added the specified number of grams of the carboxy silicone and 140.0 grams of salicylic acid and 0.25% of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is used without additional purification.

EXAMPLE 15

Into a suitable round bottom, three neck flask equipped with a Dean Stark trap, a thermometer and a nitrogen sparge is added the specified number of grams of the carboxy silicone), 74.0 grams of example 1, and 140.0 grams of the salicylic acid and 0.25% of total weight of the batch of catalyst. The reaction mass is blanketed with nitrogen, and heated to 180 and 200 C. under an inert nitrogen blanket. Once the reaction temperature reaches 120 C. Water begins to boil off and is collected in the Dean Stark Trap. Within four to five hours the theoretical water is collected off and the acid value is very low. The product is used without additional purification.

EXAMPLE 16–28

Example 15 is repeated only this time substituting the specified number of grams of the specified carboxy silicone for the carboxy silicone specified in example 14.

| | Carboxy Silicone Compound | |
|---|---|---|
| Example | Example | Grams |
| 15 | 1 | 2,429.0 |
| 16 | 2 | 2,147.0 |
| 17 | 3 | 5,398.0 |
| 18 | 4 | 533.0 |
| 19 | 5 | 4,723.0 |
| 20 | 6 | 3,083.0 |
| 21 | 7 | 3,648.8 |
| 22 | 8 | 1,722.4 |
| 23 | 9 | 1,288.0 |
| 24 | 10 | 6,100.0 |
| 25 | 11 | 10,115.0 |
| 26 | 12 | 50,269.0 |
| 27 | 13 | 86,185.0 |
| 28 | 14 | 2,645.0 |

The compounds of the present invention are hydrophobic ultra violet absorbing compounds that are durable to many substrates like textile fabrics, fibers, skin, hair, rubber and plastics. The presence of the polyoxyalkylene groups in the molecule cause the product to be soluble in a variety of polar and non-polar solvents. These range from mineral oil, when no x, y and z are z to water when x+z is greater than 10.

What is claimed:

1. A silicone ester which conforms to the following structure:

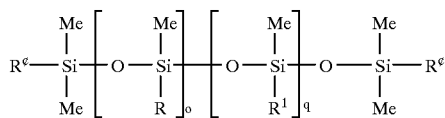

wherein;

Me is methyl; R and R' are selected from methyl and

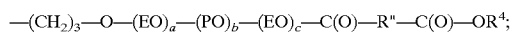

with the proviso that both R and R' are not methyl; R" is selected from

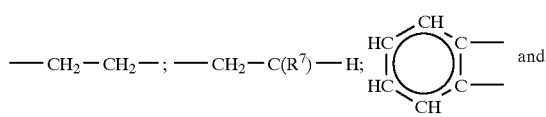

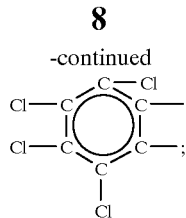

$R^7$ is alkyl having from 1 to 20 carbon atoms;

$R^1$ is selected from lower alkyl $CH_3(CH)_n$— or phenyl; n is an integer from 0 to 8; a, b and c are integers independently ranging from 0 to 20;

EO is—$(CH_2CH_2$—O)—; PO is—$(CH_2CH(CH_3)$—O)—; o is an integer ranging from 1 to 100; q is an integer ranging from 0 to 500;

$R^4$ is

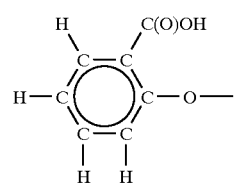

2. A compound of claim 1 wherein R" is—$CH_2$—$CH_2$—.

3. A compound of claim 1 wherein R" is—$CH_2$—$C(R^7)$—H.

4. A compound of claim 1 wherein R" is

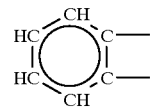

5. A compound of claim 1 wherein R" is

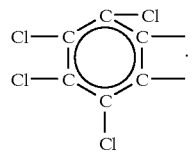

6. A compound of claim 3 wherein $R^7$ is alkyl having from 6 to 20 carbon atoms.

7. A compound of claim 3 wherein $R^7$ is alkyl having from 12 to 20 carbon atoms.

8. A compound of claim 1 wherein R' is methyl.

9. A compound of claim 1 wherein R' is

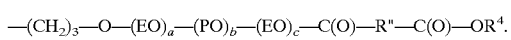

10. A compound of claim 2 wherein R' is

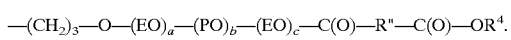

11. A compound of claim 3 wherein R' is

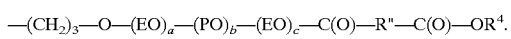

12. A compound of claim 4 wherein R' is $-(CH_2)_3-O-(EO)_a-(PO)_b-(EO)_c-C(O)-R''-C(O)-OR^4.$

13. A compound of claim 1 wherein R $-(CH_2)_3-O-(EO)_a-(PO)_b-(EO)_c-C(O)-R''-C(O)-OR^4.$

14. A compound of claim 3 wherein R is $-(CH_2)_3-O-(EO)_a-(PO)_b-(EO)_c-C(O)-R''-C(O)-OR^4.$

15. A compound of claim 5 wherein R is $-(CH_2)_3-O-(EO)_a-(PO)_b-(EO)_c-C(O)-R''-C(O)-OR^4.$

16. A compound of claim 4 wherein R is $-(CH_2)_3-O-(EO)_a-(PO)_b-(EO)_c-C(O)-R''-C(O)-OR^4.$

* * * * *